United States Patent [19]
Dhuique-Mayer et al.

[11] Patent Number: 5,718,913
[45] Date of Patent: Feb. 17, 1998

[54] RESERVOIR WHICH CAN BE IMPREGNATED WITH A SOLUTION OF ACTIVE PRINCIPLE, FOR AN IONTOPHORETIC DEVICE FOR TRANSDERMAL DELIVERY OF MEDICINAL PRODUCTS AND METHOD OF MANUFACTURE OF SUCH A RESEVOIR

[75] Inventors: Daniel Dhuique-Mayer; Laurent Liorzou, both of Dijon, France

[73] Assignee: Laboratoires D'Hygiène et Et De Diététique (L.H.D.), Paris, France

[21] Appl. No.: 600,916

[22] PCT Filed: Aug. 3, 1994

[86] PCT No.: PCT/FR94/00974

§ 371 Date: Feb. 26, 1996

§ 102(e) Date: Feb. 26, 1996

[87] PCT Pub. No.: WO95/06496

PCT Pub. Date: Mar. 9, 1995

[30] Foreign Application Priority Data

Aug. 30, 1993 [FR] France .................. 93/10360

[51] Int. Cl.⁶ .................................. A61F 13/00
[52] U.S. Cl. .................. 424/449; 424/448; 424/489; 604/20
[58] Field of Search .................. 424/449, 448, 424/489; 604/20

[56] References Cited

U.S. PATENT DOCUMENTS

| | | | |
|---|---|---|---|
| 4,474,570 | 10/1984 | Auria | 604/20 |
| 4,777,954 | 10/1988 | Keusch | 128/640 |
| 4,989,607 | 2/1991 | Keusch | 128/640 |
| 5,069,908 | 12/1991 | Henley | 424/449 |
| 5,162,043 | 11/1992 | Lew | 604/20 |
| 5,306,504 | 4/1994 | Lorenz | 424/449 |
| 5,338,490 | 8/1994 | Dietz | 252/500 |

FOREIGN PATENT DOCUMENTS

0409067A2  11/1990  European Pat. Off. .
9210235    6/1992   WIPO .

*Primary Examiner*—D. Gabrielle Phelan
*Attorney, Agent, or Firm*—Watson Cole Stevens Davis, P.L.L.C.

[57] ABSTRACT

The reservoir loaded with a divided material which can be impregnated with the solution of active principle, comprises a) a support sheet (1) made of a cavitied material which is permeable to the solution and capable of contributing to the mechanical strength of the reservoir b) a layer (3) of particles of the impregnatable material and c) a substrative layer (2) interposed between one face of the support sheet (1) and the layer of particles (3) in order to hold the latter on the support sheet (1), this substrative layer (2) consisting of a substance which is miscible with the solution of active principle.

22 Claims, 1 Drawing Sheet

U.S. Patent     Feb. 17, 1998     5,718,913
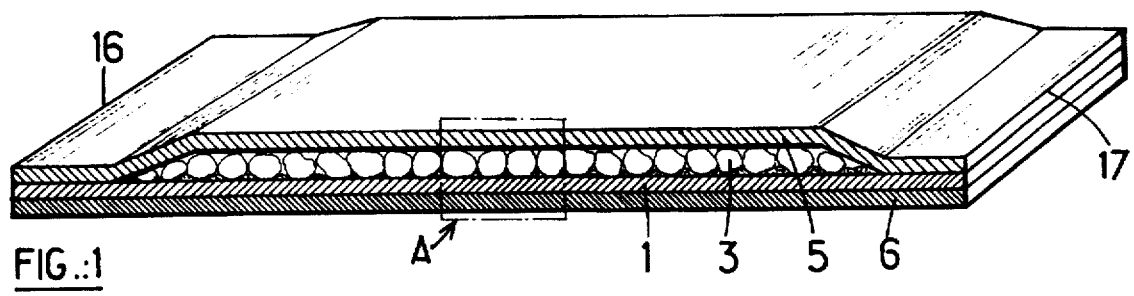
FIG.:1
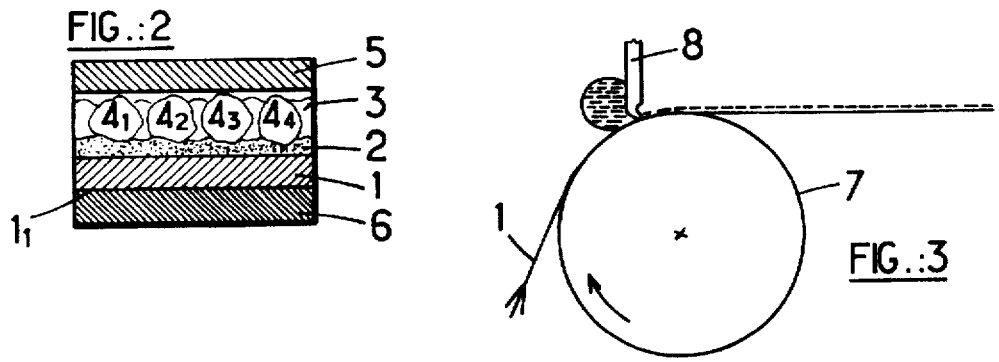
FIG.:2
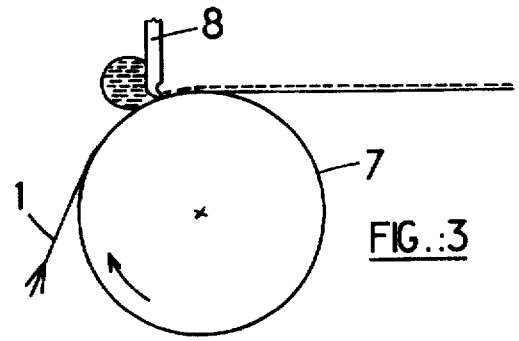
FIG.:3
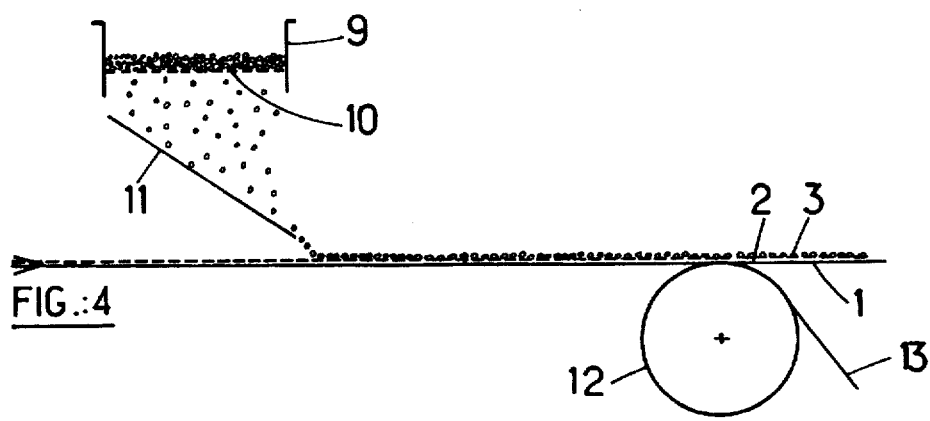
FIG.:4
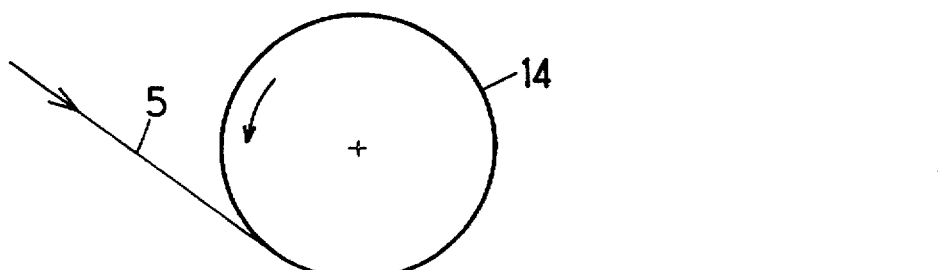
FIG.:5
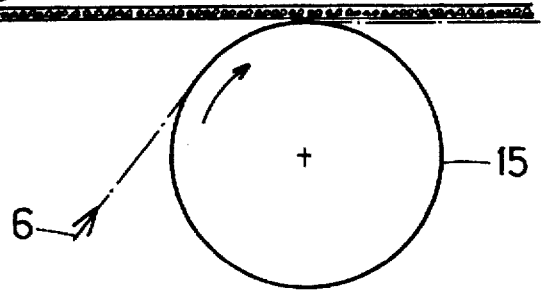

RESERVOIR WHICH CAN BE IMPREGNATED WITH A SOLUTION OF ACTIVE PRINCIPLE, FOR AN IONTOPHORETIC DEVICE FOR TRANSDERMAL DELIVERY OF MEDICINAL PRODUCTS AND METHOD OF MANUFACTURE OF SUCH A RESEVOIR

The present invention relates to a reservoir which can be impregnated with a solution of active principle in order to be used in an iontophoretic device for transdermal delivery of medicinal products and, more particularly, to such a reservoir loaded with a divided material which can be impregnated with this solution. A further object of the present invention is to provide a method of manufacture of such a reservoir.

Transdermal delivery of medicinal products assisted by iontophoresis is a technique which is currently well known, which has formed the subject matter of numerous publications such as, for example, European Patent Application No. 409067 and International Patent Application WO 92/10235, to which reference may be made for further details concerning the essential characteristics of this medical technique.

This technique consists in applying against the skin of a patient a reservoir of an active principle in solution and in forcing passage through the skin of an ionized form of this active principle, by the action of a suitably oriented electric field. In order to do this, a plane electrode is plated onto the reservoir and an electrical potential difference is set up between this electrode and a neighbouring electrode, optionally plated directly onto the skin of the patient. The electrode plated on top of the reservoir is polarized so as to expel the ions of the active principle under the skin of the patient so they pass into the vascular system of this patient.

In the current state of the art, the reservoir commonly consists of a hydrogel which can be impregnated with the solution of active principle. It is not permanently loaded with this solution. It is actually kept in the "dry" state in order to avoid problems of stability, for example those resulting from contamination and/or incompatibility of materials, and it is impregnated with the solution immediately before use.

For convenience of this use, it is then necessary for impregnation of the hydrogel contained in the reservoir to take place rapidly, in a time period of the order of one minute, for example. Impregnation of the hydrogel should also be homogeneous and complete.

The precise object of the invention is to produce such a reservoir, exhibiting rapid, complete and homogeneous loading.

A further object of the present invention is to provide a method of manufacture of such a reservoir which can be exploited industrially, that is to say a method which can provide a large production volume at a manufacturing cost price which is limited to the greatest possible extent.

The object of the invention, as well as others which will emerge on reading the following description, are achieved with a reservoir loaded with a divided material which can be impregnated with a solution of active principle, which is noteworthy in that it comprises a) a support sheet made of a cavitied material which is permeable to the solution and capable of contributing to the mechanical strength of the reservoir, b) a layer of particles of the impregnatable material, and c) a substrative layer interposed between one face of the support sheet and the layer of particles in order to hold the latter on the support sheet, this substrative layer consisting of a substance which is miscible with the solution of active principle.

The use of such an impregnatable particulate material makes it possible to provide a large area for absorption of the solution of active principle, which accelerates impregnation of the reservoir. The thickness of the layer of particles is preferably of the order of magnitude of the mean size of these particles, which ensures rapid and homogeneous spreading of the solution in the reservoir. Miscibility of the substrative layer with the solution of active principle which is to impregnate the reservoir ensures electrical continuity between this reservoir and an electrode designed to receive it.

In order to be fixed on such an electrode belonging to an iontophoretic device for transdermal delivery of medicinal products, the reservoir may be lined with a double-sided adhesive sheet, bonded to the support sheet on that face of the latter which is opposite the face coated with the substrative layer, this adhesive sheet being regularly openworked in order to ensure electrical contact between the solution and the electrode.

According to the invention, the substrative layer of the reservoir preferably consists of one of the substances in the group formed by glycerol, diacetin, homoacetin, polyethylene glycol.

According to the invention, furthermore, the impregnatable divided material which lines the reservoir is preferably chosen from cellulosic derivatives such as hydroxypropylmethylcellulose, hydroxyethylcellulose, hydroxypropylcellulose, carboxymethylcellulose, methylcellulose, polymers and copolymers of acrylic acid, of methacrylic acid, and of their esters, polyalkylene glycol gels, polyvinylpyrrolidone and its derivatives, polyvinyl alcohol, polyacrylamide and derivatives, natural gums, hydrosoluble amylaceous derivatives and copolymers (methylvinylether/maleicanhydride).

The invention also provides a method of manufacture of the reservoir according to the present invention, noteworthy in that a) a face of the support sheet is coated with an adhesive layer of a substrative product and b) the layer thus formed is powdered with particles of the material which can be impregnated with the solution of active principle. The support sheet takes the form of a band moving through a station for coating one face of this band with the substrative product, then through a station for powdering the layer of this product formed on the band. According to a preferred embodiment of the present invention, the band is powdered by sieving the particles of the impregnatable material above the adhesive substrative layer.

The band thus manufactured moves at high speed through a manufacturing machine, which ensures a large production volume at low cost. The band is then automatically welded and cut and the pieces obtained constitute reservoirs according to the invention.

BRIEF DESCRIPTION OF THE DRAWINGS

Other characteristics and advantages of the present invention will emerge on reading the following description and on inspecting the attached drawing, in which:

FIG. 1 is a perspective and sectional view of a preferred embodiment of the reservoir according to the invention, FIG. 2 is an enlarged view of the detail labelled A in FIG. 1, which shows the various product layers constituting the reservoir according to the invention, and FIGS. 3, 4 and 5 are diagrams of various stations in a machine designed for implementing the method according to the invention for manufacturing the reservoir of FIGS. 1 and 2.

As represented in FIG. 1, the reservoir according to the invention takes the form of a flat, rectangular piece, typically having an area of 6 cm×2 cm, for example. It must comprise a material which can be impregnated with a solution of active principle and must be capable of holding from 1 to 2 ml of this solution, for example.

For this purpose, the reservoir essentially comprises a support sheet 1 made of a cavitied material, impregnated with a layer 2 of substrative substance deposited on one face of the sheet 1 and having a surface capable of holding by adhesion a layer 3 of particles of a divided material which can be impregnated with a solution of active principle.

The adhesive layer 2 itself impregnates the cavities of the support sheet 1, which ensures good adhesion of this layer onto this sheet. The particles $4_1, 4_2, 4_3, 4_4$, etc. of the impregnatable material are evenly distributed over the adhesive layer 2 and held by this layer in this distribution.

The layer 3 thus provides a large absorption area, by virtue of the sum of the areas of the particles, when it is impregnated with a solution of active principle. Absorption of this solution is thereby greatly accelerated.

Uniform spreading of the solution in the layer is also promoted by the small thickness, of the order of magnitude of the mean diameter of the particles, and the flatness of this layer.

According to a first embodiment of the reservoir according to the invention, this reservoir may consist only of the layers 1, 2 and 3.

However, according to a preferred embodiment, the cohesion of the reservoir is reinforced by a cover sheet 5 which covers the layer of the particles $4_i$ in order to ensure that the latter remain held correctly against the support sheet 1.

The reservoir thus constituted must be fixed, on the side of the support sheet 1, on an electrode formed, for example, by a conductive layer of silver/silver chloride. This fixing is expediently carried out using a double-sided adhesive sheet initially attached either to the reservoir or to the electrode.

According to the invention, adhesion of this sheet on the reservoir is improved by plating on the face $1_1$ of the support sheet 1 a sheet 6 made of open-worked material such as a fine mesh, made of an electrically insulating material. The sheet 6 is welded to the support sheet at the ends of the latter adjacent to its transverse edges 16, 17, as is the cover sheet 5. One face of the double-sided adhesive sheet (not shown) is bonded against the sheet 6 which is itself plated against the support sheet 1, the other face of the adhesive sheet being intended to be applied against the surface of the electrode.

It will be noted that, in the absence of the mesh, the adhesive sheet could not adhere to the support sheet, impregnated with glycerol, for example, constituting the substrative surface, as will be seen further on. Cohesion of the entire reservoir is ensured by the welds formed in the vicinity of the edges 16, 17.

The electrical continuity of the reservoir, from the cover sheet 5 to the electrode adhering to the mesh 6, is ensured by using cavitied materials for constituting the sheets 1 and 5 and a substrative layer 2 which is miscible with the solution of active principle. This solution is injected into the reservoir using a syringe, for example, just before applying the reservoir/electrode assembly onto the skin of a patient, with a view to transthermal delivery of medicinal products assisted by iontophoresis. The solution then impregnates the particles $4_i$, the substrative layer 2 and the cavitied sheets 1 and 5. The double-sided adhesive sheet which fixes the reservoir onto the electrode can be for example made with a support of electrically conducting adhesive products. Electrical continuity to the adhesive sheet may also be obtained by open-working the said sheet so that the solution of active principle can wet the electrode through this sheet.

Various materials can be used for constituting the sheets or layers 1 to 6. Thus, in the case of the support sheet 1 and (optional) cover sheet 5, it is proposed according to the invention to use a woven or non-woven material, a felt, a mesh or an open-pored plastic foam sheet, of small thickness. This material must be sufficiently fine and open-worked, with grammage preferably lying between 10 and 50 $g/m^2$ and preferably of the order of 15 $g/m^2$, in order for a gel formed by the particles $4_i$ impregnated with the solution of active principle to be capable of passing through it. The substances constituting the sheets 1 and 5 are preferably polymers: polyethylene, polypropylene, polyamide, polyester, polyurethane, cellulose, viscose, olefinic copolymer, polyvinyl chloride, cellulosic, acrylic or methacrylic polymer.

The substrative layer 2 with which the support sheet 1 is impregnated consists of a liquid which is miscible with the aqueous solution of active principle. This liquid must be sufficiently viscous so that it does not flow from the support sheet 1 which it impregnates, and sufficiently adhesive to hold the absorbent particles $4_i$ deposited on the surface of this support sheet thus impregnated. Its viscosity preferably lies between 100 and 1000 cps. For this purpose, use may be made of glycerol, diacetin, homoacetin, a polyethylene glycol (or polyoxyethylene) having low molecular mass, or any substance exhibiting equivalent characteristics which the person skilled in the art will be able to identify and choose using his normal knowledge.

The substance constituting the absorbent particles $4_i$ is preferably chosen from hydrophilic or hydrosoluble polymers. It is then in the form of powder, flakes or fibres. This divided form promotes distribution of the liquid by capillary action at the surface of the electrode. This substance is chosen from the following, taken separately or in a mixture:

cellulosic derivatives such as hydroxypropylmethylcellulose, hydroxyethylcellulose, hydroxypropylcellulose, carboxymethylcellulose, methylcellulose, polymers and copolymers of acrylic acid, of methacrylic acid and of their esters which are super-absorbent, polyethylene glycol, polypropylene glycol, polyvinyl pyrrolidone and derivatives, polyvinyl alcohol, polyacrylamide and derivatives, natural gums, guar gum, xanthan gum, pectin, carrageenan, carob flour, polysaccharides in general, hydrosoluble amylaceous derivatives, copolymers (methylvinylether/maleicanhydride).

The particles $4_i$ may also be obtained by grinding a solid layer made from a mixture of the abovementioned products, optionally with the addition of hydrophilic textile fibres such as cotton. This technique is preferred to the direct deposition on the support sheet 1, duly coated with substrate, of a mixture of various substances and textile fibres.

According to the invention, the particles obtained preferably have a mean diameter lying between 80 μm and 250 μm, and they are deposited in a fine layer of approximately 300 μm with a grammage of 30 to 250 $g/m^2$, on a substrative layer having a thickness varying between 100 and 200 μm.

It has been observed that depositing a substrative layer such as glycerol on a cavitied support sheet, for example made of a non-woven fabric, produces some degree of surface unevenness of this layer which, to some extent, "copies" the uneven cavitied surface on which it has been deposited. In order to overcome this drawback, according to the present invention, the non-woven sheet may be coated with a polyoxyethylene hydrogel or other equivalent substance, prior to deposition of the glycerol layer. In order to do this, the support layer 1 may be arranged on a peel-off protective sheet, such as silicone-coated paper, so as to give the whole sufficient mechanical strength. The sheet is then coated by any of the known coating techniques, using a roller, scraper, etc. and the non-woven sheet thus coated is then dried. After removal of the silicone-coated paper, the result is that the two faces of the support sheet have a very smooth surface. For this purpose, use may be made of a polyoxyethylene hydrogel having a molecular mass of 300000, marketed by the Belgian company JANSSEN CHEMICA, in a 2% solution. The thus smoothed surface of the non-woven fabric may then receive a glycerol layer of even thickness and good surface condition.

Reference is now made to FIGS. 3 to 5 of the attached drawing in order to describe a preferred method of manufacture of the reservoir according to the present invention. According to this method, a layer of substrative product, for example glycerol, at a ratio of approximately 75 g/m$^2$, is first of all deposited on the support sheet 1. In order to do this, a band of the material, for example non-woven, constituting the support sheet 1 is formed and it is lined with a conforming band of peel-off silicon-coated protective paper which reinforces its mechanical strength. The band can then be passed through a glycerol-coating station. FIG. 3 diagrammatically represents such a station. The band of the support sheet 1 and its silicon-coated paper are driven by a motorized roller 7 under a scraper 8 which regulates the thickness of the layer by retaining a meniscus of glycerol forming a reserve, replenished by means (not shown) well known to the person skilled in the art.

Clearly, other known coating techniques might be used instead of those illustrated in FIG. 3. Thus, the procedure may involve coating with a transfer roll, by calendering, by pad application, by spraying, or by various techniques used in printing such as, for example, the silk-screen process.

The glycerol-coated band is driven through a powdering station such as, for example, that represented in FIG. 4. The latter comprises a hopper 9, the bottom of which is closed by a sieve 10, optionally a vibrating sieve. A dehydrated powdered hydrogel, constituting the material, impregnatable with solution of active principle, of the reservoir according to the invention, is arranged in the hopper. The powder falls from the sieve onto a ramp 11 which distributes the powder evenly over the surface of the glycerol layer formed on the band of the support sheet 1 which is moving under this ramp, by virtue of the driving force developed by a motorized roller 12. The latter is also used to peel off the band 13 of silicon-coated paper which supports the band 1 until then. This band 1, lined with the layer 3 of powdered hydrogel fixed on the surface of the glycerol layer, then passes through the station represented in FIG. 5 in order to be "complexed" with a cover band 5, at a roller 14, and a band of the sheet 6, at a roller 15, assuming that such elements 5, 6 are incorporated with the reservoir according to the invention.

Bonding of the bands of sheets 1, 5 and 6 together might be reinforced by various techniques such as welding by hot calendering at points regularly distributed over the surface of the bonded bands, or assembling them by similarly distributed spots of adhesive.

The complex band thus formed is finally heat-sealed or welded at the transverse edges 16 and 17 of each reservoir manufactured (see FIG. 1), then cut at each of these edges in order to separate each reservoir. It will be noted that it is not necessary to weld this reservoir on all four edges.

The method of manufacture described hereinabove, which employs a continuously moving band, welded and cut automatically, allows high production rates and therefore low production costs, according to the aims stated in the preamble of the present description.

Clearly, the invention is not limited to the embodiments described and represented, which were given solely by way of example. Thus, powdering techniques other than sieving might be used, for example, blowing the powder through nozzles, passing the coated band of the product with adhesive surface through a fluidized powder bed, etc. Similarly, the reservoir may be formed integrally with the electrode and the double-sided adhesive may be used to plate one onto the other.

We claim:

1. Reservoir which can be impregnated with a solution of active principle in order to be used in an iontophoretic device for transdermal delivery of medicinal products, the reservoir, loaded with a particulate material impregnable with the solution, comprising:
   a) a support sheet permeable to the solution,
   b) a layer of particles of the impregnatable material, and
   c) a substrative layer interposed between one face of the support sheet and the layer of particles in order to hold the latter on the support sheet, this substrative layer consisting of a substance which is miscible with the solution of active principle.

2. Reservoir according to claim 1, characterized in that the thickness of the said layer of particles is of the order of magnitude of the mean size of these particles.

3. Reservoir according to claim 1, characterized in that it is lined with a double-sided adhesive sheet, bonded to the support sheet on a face of the latter which is opposite the face coated with the substrative layer.

4. Reservoir according to claim 3, characterized in that the said adhesive sheet is bonded by its other face onto a metal layer constituting an electrode.

5. Reservoir according to claim 3, characterized in that a sheet of porous material is interposed between the support sheet and the double-sided adhesive sheet.

6. Reservoir according to claim 1, characterized in that the support sheet is impregnated with a polyoxyethylene hydrogel.

7. Reservoir according to claim 1, characterized in that it comprises a cover sheet, covering the layer of particles of the impregnatable material.

8. Reservoir according to claim 3, characterized in that the sheets and layers forming it conform and are welded to one another by the edges.

9. Reservoir according to claim 1, characterized in that the support sheet is made of one of the products selected from the group consisting of woven or non-woven products, a felt, a mesh, a cavitied foam, made of a polymer selected from the group consisting of polyethylene, polypropylene, polyamides, polyesters, polyurethane, cellulose, viscose, olefinic copolymers, polyvinyl chloride, cellulosic, acrylic and methacrylic polymers.

10. Reservoir according to claim 1 characterized in that the substrative layer is selected from the group consisting of glycerol, diacetin, homoacetin, and polyethylene glycol.

11. Reservoir according to claim 1, characterized in that the inpregnatable divided material consists of one of the substances selected from the group consisting essentially of hydroxypropylmethylcellulose, hydroxyethylcellulose, hydroxypropylcellulose, carboxymethylcellulose, methylcellulose, polymers and copolymers of acrylic acid, of methacrylic acid and of their esters, polyalkylene glycol gels, polyvinylpyrrolidone, polyvinyl alcohol, polyacrylamide, natural gums hydrosoluble-starch compounds and copolymers (methylvinylether/maleic-anhydride).

12. Reservoir according to claim 11, characterized in that the impregnatable material consists of 80 µm to 250 µm particles, the layer of this material deposited on the substrative layer having a maximum thickness of approximately 300 µm.

13. Reservoir according to claim 7, characterized in that the cover sheet and the support sheet consist of polymer substances selected from the group consisting of polyethylene, polypropylene, polyamides, polyesters, polyurethane, cellulose, viscose, olefinic copolymers, polyvinyl chloride, cellulosic, and acrylic or methacrylic polymers.

14. Reservoir according to claim 5, characterized in that the sheet of porous material consists of a mesh, a felt, a woven or non-woven product made of polymer material.

15. Method of manufacture of a reservoir which can be impregnated with a solution of active principle in order to be used in an iontophoretic device for transdermal delivery of medicinal products, this reservoir, loaded with a divided material impregnatable with this solution, comprising: a) a support sheet made of a material which is permeable to the solution and contributing to the mechanical strength of the reservoir, b) a layer of particles of the impregnatable material, and c) a substrative layer interposed between one face of the support sheet and the layer of particles in order to hold the latter on the support sheet, this substrative layer consisting of a substance which is miscible with the solution of active principle, characterized in that (a) a face of the support sheet (1) is coated with an adhesive layer of a substrative product and (b) the layer thus formed is powdered with particles of the material which can be impregnated with the solution of active principle.

16. Method according to claim 15, characterized in that the support sheet (1) takes the form of a band moving through a first station for coating one face of band with the substrative substance, then through a second station for coating the layer of this substance formed on the band with the impregnable particles.

17. Method according to claim 16, characterized in that the moving band is lined with a band of a peel-off protective material.

18. Method according to claim 17, characterized in that the lined band is impregnated with a polyoxyethylene hydrogel, then dried, before passing through the station for coating with the substrative substance.

19. Method according to claim 17, characterized in that, at the exit of the coating station the protective band is peeled off and the substrate particle coated band is then pressed between a cover band made of an porous material covering the layer (3) of powder and a mesh band applied against the other face of the substrate- and -particle coated band.

20. Method according to claim 19, characterized in that the band product obtained is evenly welded to the final dimensions of a reservoir then cut out along these welds in order to separate each reservoir.

21. Method according to claim 19, characterized in that the band product obtained is hot-calendered in order to reinforce its cohesion.

22. Method according to claim 15, characterized in that the particles of the impregnatable material are sieved in order to form a layer of such particles on the adhesive substrative layer.

* * * * *